United States Patent [19]

Madappally et al.

[11] 4,242,446

[45] Dec. 30, 1980

[54] METHOD FOR DETERMINING A SUBSTANCE IN A BIOLOGICAL FLUID AND REAGENT COMBINATION FOR USE IN THE METHOD

[75] Inventors: Mathew M. Madappally, Cooper City, Fla.; Giovanni Bucolo, Cupertino, Calif.

[73] Assignee: Coulter Electronics, Inc., Hialeah, Fla.

[21] Appl. No.: 927,973

[22] Filed: Jul. 26, 1978

[51] Int. Cl.$^3$ .......................... C12Q 1/52; C12Q 1/34; C12Q 1/40; C12Q 1/32

[52] U.S. Cl. ........................................ 435/15; 435/16; 435/18; 435/22; 435/25; 435/26; 435/184; 435/810

[58] Field of Search .................. 195/103.5 R, 103.5 S, 195/103.5 C, 99; 435/14, 18, 16, 22, 25, 26, 810, 184; 23/230 B

[56] References Cited

U.S. PATENT DOCUMENTS

| | | | |
|---|---|---|---|
| 3,838,011 | 9/1974 | Hngen et al. | 435/14 |
| 3,925,018 | 12/1975 | Saunders | 23/230 B |
| 3,956,069 | 5/1976 | Allain et al. | 195/103.5 C |
| 4,000,042 | 12/1976 | Adams | 195/103.5 C |
| 4,086,142 | 4/1978 | Huang et al. | 195/103.5 R |

OTHER PUBLICATIONS

Madappally et al., "Enzymatic Determination of Serum Amylase", *Clin. Chem.*, vol. 22, No. 7, (1976) p. 1164.
Proelss et al., "New, Simple Maltogenic Assay for Mechanized Determination of Alpha-Amylase Activity in Serum and Urine", *Clin. Chem.*, vol.21, No. 6 (1975) pp. 694–702.

*Primary Examiner*—Thomas G. Wiseman
*Attorney, Agent, or Firm*—Silverman, Cass & Singer, Ltd.

[57] ABSTRACT

An improvement in a method for determining a substance present in a biological fluid by oxidizing a compound produced in the course of the determination in the presence of a dehydrogenase enzyme with the simultaneous production of reduced beta-nicotinamide adenine dinucleotide in an amount proportional to the content of the substance in the fluid, which fluid also contains an endogenous material which or a derivative of which produced during the determination likewise is oxidized in the presence of the enzyme with the simultaneous production of reduced beta-nicotinamide adenine dinucleotide, thereby interfering with the determination, which improvement involves first carrying out the oxidation-reduction reaction of the endogenous material or its derivative, then oxidizing the resulting reduced beta-nicotinamide adenine dinucleotide in the presence of lactate dehydrogenase with the simultaneous reduction of pyruvate to lactate, thereafter inhibiting the lactate dehydrogenase enzymatic activity, and thereafter producing a quantity of the aforesaid compound produced in the course of the determination for conducting the oxidation-reduction reaction therewith without interference caused by the endogenous material or the lactate dehydrogenase. Substances which may be determined include alpha-amylase, transaminases, and triglycerides. A two-reagent combination is employed for the determination.

21 Claims, No Drawings

METHOD FOR DETERMINING A SUBSTANCE IN A BIOLOGICAL FLUID AND REAGENT COMBINATION FOR USE IN THE METHOD

BACKGROUND OF THE INVENTION

This invention relates to a method for the quantitative determination or assay of a substance present in a biological fluid, especially in human blood serum. More particularly, the invention relates to a method in which a compound produced in the course of the determination is oxidized in an enzymatic oxidation-reduction reaction with simultaneous production of reduced beta-nicotinamide adenine dinucleotide in an amount proportional to the content of the substance in the fluid, and to an improvement for obviating the interference caused by another substance in the fluid which while not related quantitatively to the substance being determined undergoes an enzymatic oxidation-reduction reaction with the production of reduced beta-nicotinamide adenine dinucleotide and thus reduces the accuracy of the determination. The invention also relates to a reagent combination for use in the method.

A number of metabolites present in biological fluids may be determined advantageously by methods in which beta-nicotinamide adenine dinucleotide in its oxidized form (NAD), is converted in an enzymatic oxidation-reduction reaction to its reduced form (NADH) proportionally to the content of the substance being determined. The NADH may be determined quantitatively by measurement of the intensity of light absorption, preferably at the absorption maximum of 340 nanometers (nm.). Alternatively, the NADH produced may be reacted with 2-p-iodophenyl-3-p-nitrophenyl-5-phenyl tetrazolium chloride (INT) in an enzymatic oxidation-reduction reaction, to convert the INT to its reduced form (INTH). The INTH may be determined quantitatively by measurement of light absorption, preferably at the absorption maximum of 500 nm.

Substances which may be determined by the foregoing procedure include the enzyme alpha-amylase, transaminase enzymes including glutamate oxalacetate transaminase (GOT) and glutamate pyruvate transaminase (GPT), and triglycerides. The procedure is especially useful for making determinations in human blood serum, including the serum content of plasma, and also in other biological fluids, including, for example, urine, duodenal fluid, and peritoneal fluid.

The foregoing procedure potentially is very attractive. However, the biological fluids contain endogenous materials other than the substances being determined, which themselves or the derivatives of which as produced during the determination participate in enzymatic oxidation-reduction reactions with the formation of NADH, thereby interfering with the determinations. As an example, alpha-amylase in a biological fluid, particularly human blood serum, is determined in existing procedures by allowing the enzyme to hydrolyze starch to maltose, after which the maltose is enzymatically hydrolyzed to glucose, the glucose is converted to glucose-6-phosphate, and the latter compound is reacted with NAD in an oxidation-reduction reaction to produce NADH. Endogenous glucose also present in the fluid participates in the latter reactions with the production of non-specific NADH, not related to the alpha-amylase activity, which reduces the accuracy of the determination to the extent of its presence.

While methods have been proposed for removing the endogenous glucose, as described in Clin. Chem., 21, 694 (1975) and Clin. Chem., 21, 947 (1975), they suffer from disadvantages, including, inter alia, lack of simplicity and convenience as desired for laboratory procedures, and, particularly, for use as an emergency hospital diagnostic tool.

U.S. Pat. No. 4,000,042 discloses a method in which endogenous glucose initially is consumed, with the production of NADH, after which alpha-glucosidase is added to initiate the assay reactions. Employing such a method, it is possible for the absorbance due to alpha-amylase activity to be negligible compared to the absorbance due to endogenous glucose, thus leading to inaccurate results. Also, many of the available instruments for measuring absorbances are incapable of measuring high absorbances such as can be obtained with high endogenous glucose concentrations.

As another example, the activity of GOT and GPT in serum may be determined, based on the measurement of the concentration of glutamate formed in transaminase reactions, by oxidative deamination with simultaneous reduction of NAD to NADH, followed by reduction of INT to INTH. The reactions are performed by incubation of the serum with a single mixed reagent. However, endogenous amino acids in the serum likewise are oxidatively deaminated with the formation of non-specific NADH. While procedures are available to correct for such unreliable results, they involve disadvantages such as increased labor, lack of adaptability to performance in automated instruments, and/or incomplete removal of interfering endogenous materials.

An additional example is the determination of triglycerides (fatty acid esters of glycerol) in serum, wherein the triglycerides are enzymatically hydrolyzed with lipase to produce glycerol, and the glycerol or glycerol phosphate produced therefrom is reacted with NAD in an oxidation-reduction reaction to produce NADH. The results are adversely affected by the presence of endogenous glycerol, which is present in varying amounts in serum. While the endogenous glycerol content can be determined using a reagent containing all of the reactants except the lipase, and subtracting the value thus obtained from the value obtained using a complete reagent including lipase, the procedure is complicated and time-consuming.

SUMMARY OF THE INVENTION

This invention relates to an improvement in a method for determining or assaying a substance present in a biological fluid, which fluid also contains an endogenous material interfering with the determination. More particularly, the substance present in the fluid is determined by oxidizing a compound produced in the course of the determination in the presence of a dehydrogenase enzyme with the simultaneous production of reduced beta-nicotinamide adenine dinucleotide in an amount proportional to the content of the substance in the fluid. The interfering endogenous material or a derivative thereof which is produced during the determination undergoes a like reaction with the production of reduced beta-nicotinamide adenine dinucleotide, which is non-specific to the substance being determined and therefore diminishes the accuracy of the determination. The improvement comprises oxidizing the endogenous material or derivative thereof in the presence of the dehydrogenase enzyme with the simultaneous reduction of beta-nicotinamide adenine dinucleotide, oxidizing the resulting reduced beta-nicotinamide adenine dinucleotide in the presence of lactate dehydrogenase with the simultaneous reduction of pyruvate to lactate, thereafter inhibiting the lactage dehydrogenase enzymatic activity, and thereafter producing a quantity of the said compound produced in the course of the determination for said oxidation thereof and simultaneous production of reduced beta-nicotinamide adenine dinucleotide in an amount proportional to the content of the substance being determined.

The improved method is applicable to various determinations employing enzymatic oxidation-reduction reactions catalyzed by dehydrogenase enzymes to produce reduced beta-nicotinamide adenine dinucleotide, such as described above, including determinations of alpha-amylase, GOT, GPT, and triglycerides.

The method can be performed rapidly and in a single vessel, such as a laboratory tube, using common laboratory equipment. The method is sensitive, requiring only a very small portion of the fluid to be determined. Lag phases, common to multiple-step or coupled enzymatic reactions, are reduced by the optimization of components and conditions. The method easily can be adapted to perform on automated instruments.

In a preferred embodiment of the method of the invention, the alpha-amylase present in a biological fluid also containing endogenous glucose is determined by (1) enzymatically hydrolyzing soluble starch with the alpha-amylase present in the fluid to produce oligosaccharides including maltose, (2) concurrently reacting the glucose present with adenosine triphosphate in the presence of hexokinase to produce glucose-6-phosphate, reacting the glucose-6-phosphate with beta-nicotinamide adenine dinucleotide in the presence of glucose-6-phosphate dehydrogenase to produce 6-phosphogluconate and reduced beta-nicotinamide adenine dinucleotide, and reacting the reduced beta-nicotinamide adenine dinucleotide with pyruvate in the presence of lactate dehydrogenase to produce beta-nicotinamide adenine dinucleotide in its oxidized form and lactate, (3) thereafter inhibiting the lactate dehydrogenase enzymatic activity and (4) subsequently continuing the hydrolysis with the alpha-amylase present, enzymatically hydrolyzing the maltose produced in the presence of alpha-glucosidase to produce glucose, reacting the glucose thus produced with adenosine triphosphate in the presence of hexokinase to produce glucose-6-phosphate, and reacting the glucose-6-phosphate thus produced with beta-nicotinamide adenine dinucleotide in the presence of glucose-6-phosphate dehydrogenase to produce reduced beta-nicotinamide adenine dinucleotide in an amount proportional to the alpha-amylase activity. Optionally, step (1) may include the enzymatic hydrolysis of the maltose produced in such step, in the presence of alpha-glucosidase, to produce glucose. The reduced beta-nicotinamide adenine dinucleotide (NADH) produced in the indicator reactions of step (4), or INTH produced by reaction of INT therewith, may be determined by measurement of light absorption, as described above.

The foregoing embodiment serves to enzymatically remove or consume endogenous glucose, small amounts of glucose present in the starch and produced by alpha-amylase, and, optionally, glucose produced by alpha-glucosidase. The embodiment is especially advantageous in that the performance of steps (1) and (2) concurrently obviates any lag period following removal of the glucose, in step (2). The indicator reactions may commence immediately thereafter, resulting in an increase in absorbance of light. The rate of this increase in absorbance (absorbance increase per minute) being directly proportional to amylase activity present in the sample, the amylase activity in the sample may be calculated with a high degree of accuracy from the rate of change of absorbance based upon the extinction coefficient of the absorbing species. In this connection, and owing to the oxidation in step (2) of the NADH resulting from the oxidation of endogenous glucose and other glucose present, the initial absorbance at 340 nm., representing the NADH produced in step (4), is close to zero, so that any absorbance resulting from alpha-amylase activity, in the range of 0–1500 Somogyi units/dl, can be measured accurately.

The invention minimizes the number of reagents and additions necessary for an accurate determination of alpha-amylase, in a relatively short period of time. The invention also provides a new and improved two-reagent combination for use in the foregoing determination. A first reagent is admixed with the fluid initially for carrying out steps (1) and (2). A second reagent is admixed with the product of steps (1) and (2) for carrying out steps (3) and (4). The reagents are described more specifically hereinafter.

DESCRIPTION OF THE PREFERRED EMBODIMENTS

The following reaction sequence conventionally may be employed for determining or assaying alpha-amylase present in a biological fluid such as human blood serum:

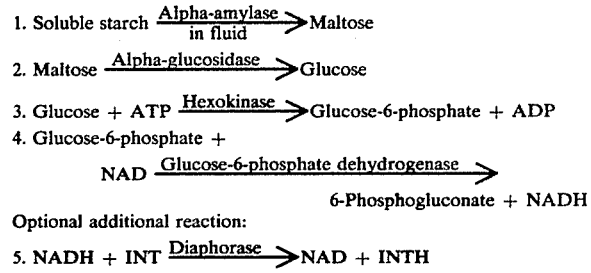

1. Soluble starch $\xrightarrow[\text{in fluid}]{\text{Alpha-amylase}}$ Maltose

2. Maltose $\xrightarrow{\text{Alpha-glucosidase}}$ Glucose

3. Glucose + ATP $\xrightarrow{\text{Hexokinase}}$ Glucose-6-phosphate + ADP

4. Glucose-6-phosphate + NAD $\xrightarrow{\text{Glucose-6-phosphate dehydrogenase}}$ 6-Phosphogluconate + NADH Optional additional reaction:

5. NADH + INT $\xrightarrow{\text{Diaphorase}}$ NAD + INTH wherein certain compounds are represented as follows:
ATP=Adenosine triphosphate
ADP=Adenosine diphosphate
NAD=Beta-nicotinamide adenine dinucleotide
NADH=Reduced form of NAD
INT=2-p-Iodophenyl-3-p-nitrophenyl-5-phenyl tetrazolium chloride
INTH=Reduced form of INT NADH or INTH, as the case may be, is measured photometrically, and the alpha-amylase activity is calculated from the results.

If endogenous glucose remains in the fluid, it will undergo reaction 3, and reactions 4 and 5 (when employed) will follow, to produce additional NADH or INTH, which is not produced as a result of alpha-amylase activity. Since the measurement of NADH or INTH does not distinguish the source of the compound, the alpha-amylase activity as calculated therefrom will be inaccurate.

In the invention, the endogenous glucose is removed or consumed by conversion to 6-phosphogluconate, employing reactions 3 and 4. The NADH next is returned to its oxidized state, to prevent interference with the determination as subsequently completed, by the following reaction:

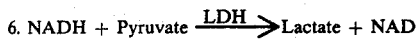
6. NADH + Pyruvate —LDH→ Lactate + NAD where LDH=Lactate dehydrogenase The lactate dehydrogenase enzyme then is inhibited or inactivated, to prevent interference with the subsequent part of the determination. Under the conditions of the determination, particularly at the pH provided in the reaction mixture, the enzyme may be inhibited by the addition of the anion of oxamic acid. Following the inhibition of the enzyme, the determination of alpha-amylase may be carried out without interference caused by the endogenous glucose, by conducting reactions 1 through 4, and, optionally, reaction 5.

In the preferred embodiment of the method, described above, reaction 1 is conducted concurrently with reactions 3, 4 and 6 as applied to the endogenous glucose, in a first phase of the determination. This procedure has the advantage of eliminating the lag period that would occur were the enzymatic hydrolysis of the starch not to commence until after inhibition of the lactate dehydrogenase enzyme. An additional advantage is that amounts of glucose present in the starch and/or produced by the starch hydrolysis are removed together with the endogenous glucose.

Optionally, reaction 2 is applied to the maltose produced from starch in reaction 1 may be allowed to proceed along with reactions 1, 3, 4 and 6 in the first phase, in which case the glucose produced from the maltose will be converted to 6-phosphogluconate along with the endogenous glucose, and the NADH produced will be oxidized to NAD with simultaneous reduction of pyruvate to lactate in reaction 6. However, it is further preferred to commence reation 2 in a second phase of the determination, following inhibition of the lactate dehydrogenase activity, at which time, reactions 1 through 4 or 1 through 5 are conducted.

With the further preferred procedure, maltose is produced in the preceding first phase in relatively small amounts, and higher oligosaccharides, having more than two glucose units, accumulate in relatively large amounts. The conditions then are favorable for conversion of the higher oligosaccharides to maltose by alpha-amylase and, hence, the indicator reactions commence without any lag period. The method is very sensitive. Another advantage of the preferred procedure is that only a very small sample and smaller quantities of the reagent materials are required.

In the further preferred procedure, the biological fluid is admixed with a first reagent which contains the materials required for conducting reactions 1, 3, 4 and 6, including soluble starch, ATP, hexokinase, NAD, glucose-6-phosphate dehydrogenase, pyruvate, and LDH. The mixture is incubated to hydrolyze starch and remove the endogenous glucose and other glucose present. The product is admixed with a second reagent which contains the anion of oxamic acid as an inhibitor of the lactate dehydrogenase enzyme activity and the alpha-glucosidase required for conducting reaction 2. The second mixture is incubated to effect reactions 1 through 4, for determining the alpha-amylase activity. If it be desired to employ reaction 5 as well, the materials required for that reaction, INT and diaphorase, also are provided in the second mixture.

The reagents are employed in aqueous solutions of water-soluble reagent materials in distilled or deionized water. Each reagent solution preferably has a pH in the range of about 6.3–7.1, more preferably, a pH of about 6.5.

A soluble starch is employed which is completely soluble in an aqueous solution of the first reagent, preferably without heating, to give a clear solution. Suitable materials are readily available, including, for example, "Soluble Starch GR," according to Zulkowsky (E. Merck Co.), "Paragon Indicator for Iodine Titration" (Eastern Chemical Co.), and "Superlose 500" (Stein-Hall and Co.), the latter being described in U.S. Pat. No. 3,888,739, being made from the amylose fraction of potato starch and containing no significant amount of the amylopectin fraction of starch.

Pyruvic acid or a water-soluble salt thereof may be employed in the first reagent to provide the desired anion of pyruvic acid in solution, it being preferred to employ an alkali metal salt of pyruvic acid, especially, the sodium or potassium salt. Oxamic acid or a water-soluble salt thereof is employed in the second reagent to provide the inhibiting anion of oxamic acid in solution. Preferably, an alkali metal oxamate, especially the sodium or potassium salt, is employed as the reagent material.

The pH is adjusted and maintained in the preferred embodiment by a buffer, which may be one of the phosphate and non-phosphate buffers known to be suitable for the purpose, such as those disclosed in U.S. Pat. No. 4,036,697 (Col. 5). It is preferred to employ a phosphate buffer, preferably, alkali metal phosphate, more preferably, potassium or sodium phosphate. The desired pH is obtained by providing monobasic and dibasic phosphate salts in a suitable ratio, e.g., by titrating a solution of monobasic phosphate against a solution of dibasic phosphate to the desired pH. Alternatively, the buffer may be prepared by adding a strong alkali such as potassium or sodium hydroxide to phosphoric acid solution, to provide the desired pH.

Materials which preferably are incorporated in the reagents but do not take part directly in the reactions include a source of chloride ions, a source of magnesium ions, and bovine serum albumin. The chloride ion acts as a cofactor for alpha-amylase and is provided in the form of a soluble salt, preferably an alkali metal salt such as sodium or potassium chloride. The magnesium ion acts as a cofactor for hexokinase and is incorporated in the form of a soluble salt, preferably a salt of a weak acid such as aspartic acid. Bovine serum albumin is employed as a bulking agent.

Where the determination includes reactions 1 through 4 and 6, the first reagent preferably contains the materials listed in Table 1, and the second reagent preferably contains the materials listed in Table 2, in relative proportions between about 80% and 120% (±20%) of the proportions indicated in each table.

TABLE 1

| Material | Amount |
|---|---|
| Soluble starch | 1.25 grams |
| Adenosine triphosphate | 1.25 millimoles |
| Beta-nicotinamide adenine dinucleotide | 2 millimoles |
| Alkali metal pyruvate | 0.75 millimoles |
| Hexokinase | 1500 I.U. |
| Glucose-6-phosphate dehydrogenase | 2500 I.U. |
| Lactate dehydrogenase | 250 I.U. |

TABLE 1-continued

| Material | Amount |
| --- | --- |
| Alkali metal phosphate buffer, pH 6.3–7.1 | 25 millimoles |
| Alkali metal chloride | 50 millimoles |
| Magnesim salt | 3 millimoles |
| Bovine serum albumin | 4 grams |

TABLE 2

| Material | Amount |
| --- | --- |
| Alpha-glucosidase | 7000 I.U. |
| Alkali metal oxamate | 180 millimoles |
| Alkali metal phosphate buffer, pH 6.3–7.1 | 25 millimoles |
| Bovine serum albumin | 4 grams |

Where the determination also includes reaction 5, 1,000 I.U. of diaphorase preferably is included in the first reagent, together with the materials set forth in Table 1, and 0.8 millimoles of INT preferably is included in the second reagent, together with the materials set forth in Table 2. The foregoing proportions may be varied within a range of ±20%. The foregoing reagents are employed in aqueous solutions of the materials, present in the amounts set forth per liter of solution.

The determination of triglycerides in human blood serum is very important because of its great diagnostic value. A conventional reaction sequence which may be employed for determining the triglycerides present in a biological fluid such as human blood serum, based on the liberation of glycerol by enzymatic hydrolysis with lipase, is as follows:

Triglycerides $\xrightarrow{\text{Lipase}}$ Glycerol + Free Fatty Acids

Glycerol + NAD $\xrightarrow{\text{GDH}}$ NADH + Dihydroxyacetone where GDH = Glycerol dehydrogenase
Alternatively, the following reactions may be employed for measurement of the glycerol liberated:

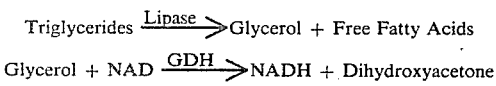

Glycerol Phosphate + NAD $\xrightarrow{\text{GPDH}}$

Dihydroxyacetone Phosphate + NADH where:
GK = Glycerokinase
GPDH = Glycerophosphate dehydrogenase In either case, reaction 5, set forth above, may be employed as an optional additional reaction, with the formation of INTH. NADH or INTH, as the case may be, is measured photometrically, and the triglyceride concentration in the biological fluid, which is directly proportional to the absorbance in either case, is calculated from the results.

The foregoing determinations are inaccurate when endogenous glycerol is present in the biological fluid, which always is the case in human serum, inasmuch as the endogenous glycerol is not discriminated. The endogenous glycerol concentration may be measured by duplicating the determination in the absence of the enzyme lipase, but this requires a complete duplicate procedure.

In the invention, the endogenous glycerol is removed or consumed in a first phase of the determination in one of two ways, depending on which of the above procedures is employed for the determination of triglycerides, employing a first reagent of a two-reagent combination and incubating. The following reactions are employed in connection with the first-described procedure, the first reagent in this case containing NAD, GDH, pyruvate, and LDH:

Endogenous Glycerol + NAD $\xrightarrow{\text{GDH}}$ NADH +

Dihydroxyacetone NADH + Pyruvate $\xrightarrow{\text{LDH}}$ Lactate + NAD

The following reactions are employed with the second-described procedure, the first reagent in this case containing ATP, GK, NAD, GPDH, pyruvate, and LDH:

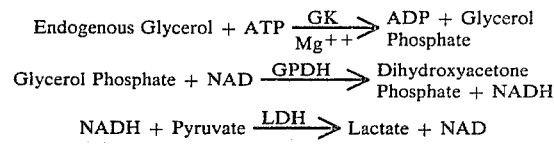

Glycerol Phosphate + NAD $\xrightarrow{\text{GPDH}}$ Dihydroxyacetone Phosphate + NADH NADH + Pyruvate $\xrightarrow{\text{LDH}}$ Lactate + NAD In each case, the last reaction is the same as reaction 6, above.

In a second phase of the determination, a second reagent is added, and the mixture is incubated. The second reagent contains lipase and LDH enzyme inhibitors, e.g., alkali metal oxamate and alkali metal oxalate. LDH is inhibited, and the above-described hydrolysis of triglycerides takes place, followed by the reaction or reactions, according to the particular procedure, resulting in the production of NADH. The (optional) incorporation of INT and diaphorase in the reaction mixture results in the production of INTH, according to reaction 5. The absorbance based on NADH production or based on INTH production is measured for determining accurately the triglyceride concentration in the biological fluid.

The determination of glutamate oxalacetate transaminase (GOT) and the determination of glutamate pyruvate transaminase (GPT) in human blood serum are very important diagnostically. An advantageous method for determining the activity of each enzyme is to employ the enzyme to convert alpha-ketoglutarate (alpha-oxoglutarate) to L-glutamate, according to the appropriate one of the following transaminase reactions, and then determine the amount of glutamate produced:

Alpha-ketoglutarate + L-Aspartate $\xrightarrow{\text{GOT}}$ L-Glutamate + Oxalacetate Alpha-ketoglutarate + L-Alanine $\xrightarrow{\text{GPT}}$ L-Glutamate + Pyruvate The glutamate is determined by means of the following reactions, after which INTH is measured colorimetrically, and the measurement thus obtained is directly proportional to the activity of the enzyme in the serum:

L-Glutamate + NAD + H$_2$O $\xrightarrow{\text{GLDH}}$ NADH + Alpha-ketoglutarate + NH$_3$ NADH + INT $\xrightarrow{\text{Diaphorase}}$ INTH + NAD where GLDH=Glutamate dehydrogenase Equilibrium conditions reqire large concentrations of GLDH, which in turn leads to oxidative deamination of certain L-amino acids found in the serum, such as glutamate, alanine, leucine, isoleucine, valine, methionine, and alpha-aminobutyrate. The reactions of these endogenous amino acids are typified by the above reaction of L-glutamate and NAD, producing non-specific NADH and an incorrect determination, i.e., falsely indicating an elevation of the enzyme activity.

Proceeding in accordance with the invention, reactive endogenous amino acids are removed or consumed in a first phase of the determination by incubating with a first reagent, to conduct the following reactions, in which L-glutamate is shown as representative of the several amino acids:

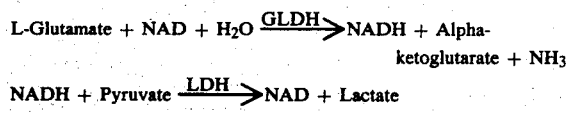

$$\text{L-Glutamate} + \text{NAD} + \text{H}_2\text{O} \xrightarrow{\text{GLDH}} \text{NADH} + \text{Alpha-ketoglutarate} + \text{NH}_3$$

$$\text{NADH} + \text{Pyruvate} \xrightarrow{\text{LDH}} \text{NAD} + \text{Lactate}$$

The latter reaction is the same as reaction 6, above. In a preferred procedure, the first reagent includes L-aspartate for GOT determination or L-alanine for GPT determination, NAD, GLDH, diaphorase, pyruvate, and LDH.

In a second phase of the determination, a second reagent is added, and the mixture is incubated. The second reagent preferably contains alpha-ketoglutarate, INT, and LDH inhibitors, e.g., alkali metal oxamate and alkali metal oxalate. LDH is inhibited, and the above-described transaminase and glutamate-determining reactions take place. Enzymatic activity is terminated at a predetermined time by acidification, and INTH is measured colorimetrically. Alternatively, the enzymatic activity may be maintained, and the rate of change of absorbance over a period of time may be determined. The foregoing improved method for determining GOT and GPT in a biological fluid is claimed in our copending application Ser. No. 933,183, filed Aug. 14, 1978.

The following examples illustrate compositions and procedures for making determinations in accordance with preferred embodiments of the invention. It will be understood that the invention is not limited to the materials, proportions, conditions and procedures set forth in the examples, which are merely illustrative.

EXAMPLE 1

Alpha-amylase activity in human blood serum is determined employing first and second reagent solutions. The first solution has a pH of about 6.5 and contains the materials set forth in Table 3 dissolved in distilled or deionized water in the proportions indicated:

TABLE 3

| Material | Amount Per Liter |
|---|---|
| Soluble starch | 1.25 grams |
| Adenosine triphosphate (ATP) | 1.25 millimoles |
| Beta-nicotinamide adenine dinucleotide (NAD) | 2 millimoles |
| Sodium pyruvate | 0.75 millimoles |
| Hexokinase | 1500 I.U. |
| Glucose-6-phosphate dehydrogenase | 2500 I.U. |
| Lactate dehydrogenase (LDH) | 250 I.U. |
| Potassium phosphate buffer, pH 6.5 | 25 millimoles |
| Sodium chloride | 50 millimoles |
| Magnesium aspartate | 3 millimoles |

TABLE 3-continued

| Material | Amount Per Liter |
|---|---|
| Bovine serum albumin | 4 grams |

The soluble starch is Soluble Starch GR according to Zulkowsky (E. Merck Co. Catalog No. 1257). The potassium phosphate buffer is a mixture of mono and dibasic potassium phosphate.

The glucose-6-phosphate dehydrogenase is from *L. mesenteroids*. Hexokinase is from yeast. Lactate dehydrogenase is from porcine heart or rabbit muscle. Commercially available bovine serum albumin, Fraction V (J.A.C.S. 68, 459 (1956)), free of contamination by carbohydrates, is employed, such as the product of U.S. Biochemical Corporation.

The second reagent solution has a pH of about 6.5 and contains the materials set forth in Table 4, including sodium oxamate inhibitor of LDH, dissolved in distilled or deionized water in the proportions indicated.

TABLE 4

| Material | Amount Per Liter |
|---|---|
| Alpha-glucosidase | 7000 I.U. |
| Sodium oxamate | 180 millimoles |
| Potassium phoshate buffer, pH 6.5 | 25 millimoles |
| Bovine serum albumin | 4 grams |

The potassium phosphate buffer and the bovine serum albumin are as set forth for the first reagent solution. The alpha-glucosidase is from yeast. The several enzymes employed in the two solutions are available from various commercial sources.

In conducting a determination, two ml. of the first reagent solution is pipetted into a cuvette, and 50 ul. (0.05 ml.) of a sample of blood serum is added. The contents are mixed and incubated at 37° C. for 10 minutes. At that time, one ml. of the second reagent solution is admixed with the resulting reaction mixture. Incubation at 37° C. is continued while the indicator reactions take place. The intensity of light absorption is measured at 340 nm. against a reagent blank, continuously for 5 minutes, to determine the rate of change of absorbance due to NADH formed. The reagent blank is prepared and incubated in the same manner as the sample mixture, except that instead of using a sample of blood serum, 50 ul. of distilled water is employed.

The alpha-amylase activity of the serum sample is calculated based upon the extinction coefficient of NADH, employing the following equation:

$$\text{Amylase activity of serum sample in I.U./l.} = \frac{\Delta A/\text{min.}}{6.22} \times \frac{\text{Total Volume}}{\text{Sample Volume}} \times 1000$$

where the total volume is the combined volume of the first and second reagents and the sample, in this case, 3.05 ml. The sample volume is 0.05 ml. $\Delta A/\text{min.}$ represents the absorbance change per minute.

Alternatively, the determination may be made by measuring the light absorption at 500 nm, in which case, the following changes are made: INT is incorporated in the second reagent solution, in a proportion of 0.8 micromole per assay, and diaphorase (from *Clostidium kluyveri*) is incorporated in the first reagent solution in a proportion of about 1 I.U. per assay. The rate of change of absorbance due to INTH formed as a result of amylase activity present in the serum sample may be compared with the rate of change of absorbance due to INTH formed as a result of amylase activity present in an alpha amylase control having known amylase activity, which is determined in the same manner, except that the control is substituted for the sample in the procedure. The activity of the serum sample is calculated employing the following equation:

$$\text{Alpha-amylase activity of serum sample} = \frac{\text{Alpha-amylase activity of control} \times \text{Rate of change of absorbance for the sample}}{\text{Rate of change of absorbance for the control}}$$

In a further alternative, instead of following the indicator reactions which produce INTH, 1 ml. of 0.4 N hydrochloric acid is added to each of the serum sample and control mixtures at a predetermined time of incubation following addition of the second reagent solution, preferably, after about 5-10 minutes of incubation. At that time, the intensity of light absorption at 500 nm by each solution is measured. The alpha-amylase activity of the serum sample is determined according to the latter equation, substituting the total absorbances for the respective rates of change of absorbance in the equation.

EXAMPLE 2

Triglycerides in human blood serum are determined employing first and second reagent solutions. The first solution has a pH of about 7.4–7.6 and contains the materials set forth in Table 5 dissolved in distilled or deionized water in the proportions indicated.

TABLE 5

| Material | Amount Per Liter |
| --- | --- |
| Glycerol dehydrogenase (GDH) | 3,000 I.U. |
| Diaphorase | 3,000 I.U. |
| Lactate dehydrogenase (LDH) | 500 I.U. |
| B-Nicotinamide adenine dinucleotide (NAD) | 4 millimoles |
| Deoxycholic acid | 0.12 millimoles |
| Potassium phosphate buffer, pH 7.4–7.6 | 100 millimoles |
| Sodium pyruvate | 0.5 millimoles |
| Trypsin inhibitor | 0.2 grams |

The glycerol dehydrogenase is from *E. aerogenes* and is commercially available. The trypsin inhibitor is added to inhibit proteases which may be present in the lipase preparation subsequently added. It is obtained from soybean and available from U.S. Biochemical Corporation. The diaphorase and LDH are from the sources indicated in Example 1.

The second reagent solution has a pH of about 7.4–7.6 and contains the materials set forth in Table 6 dissolved in distilled or deionized water in the preparations indicated.

TABLE 6

| Material | Amount Per Liter |
| --- | --- |
| Sodium oxamate | 20 millimoles |
| Potassium oxalate | 53 millimoles |
| INT | 1.0 millimoles |
| Lipase | $2 \times 10^6$ I.U. |
| Potassium phosphate buffer, pH 7.4–7.6 | 100 millimoles |
| Manganese chloride | 0.2 millimoles |

The lipase is from *Rhizopus arrhizus* or from hog pancreas. Manganese chloride is employed as an activator of glycerol dehydrogenase. The proportions of the materials in the first and second reagent solutions may vary within a preferred range of ±20% of the proportions set forth in Tables 5 and 6.

In this determination, conducted at a slightly alkaline pH, both oxamate and oxalate inhibitors of LDH activity are included in the second reagent solution, for inhibiting LDH activity in either direction in the following reaction (reaction 6):

$$\text{Pyruvate} + \text{NADH} \xrightleftharpoons{\text{LDH}} \text{Lactate} + \text{NAD}$$

The reduction of pyruvate to lactate in the presence of LDH occurs at neutral pH, and oxamate is present to inhibit this reaction. The oxidation of lactate to pyruvate in the presence of LDH occurs at an optimum pH of about 8. Oxalate inhibits this reaction, which otherwise might take place following the removal of endogenous glycerol, and also owing to the presence of endogenous lactate and LDH in the serum, which would result in the production of NADH non-specific to the triglycerides being determined.

A determination is made by incubating a mixture of 0.5 ml. of the first reagent solution and 25 ul. of a sample of serum at 37° C. for 10 minutes. At that time, 0.5 ml. of the second reagent solution is added, and incubation is continued for an additional 20 minutes. A 3 ml. quantity of 0.1 N hydrochloric acid then is added to stop the reaction.

A triglyceride control and a reagent blank are run in parallel to the serum sample. For the control, 25 ul. of a standard triglyceride solution is employed in place of the sample. For the blank, 25 ul. of distilled water is employed in place of the sample. The sample and control absorbances are measured against the reagent blank, and the triglyceride concentration in the sample is calculated as follows:

$$\frac{\text{Triglyceride concentration in control}}{\text{Absorbance of control}} \times \text{Absorbance of sample}$$

We claim:

1. In a method for determining a substance present in a biological fluid by reacting a compound produced in the course of the determination in an enzymatic oxidation-reduction reaction with beta-nicotinamide adenine dinucleotide catalyzed by a dehydrogenase enzyme to produce reduced beta-nicotinamide adenine dinucleotide in an amount proportional to the content of the substance in the fluid, said fluid also containing an endogenous material which or a derivative of which produced during the determination likewise reacts in an enzymatic oxidation-reduction reaction with beta-nicotinamide adenine dinucleotide catalyzed by said dehydrogenase to produce reduced beta-nicotinamide adenine dinucleotide, thereby interfering with the determination, the improvement for obviating the interference caused by the endogenous material which comprises:

reacting said endogenous material or derivative thereof present in said fluid in an enzymatic oxidation-reduction reaction with beta-nicotinamide adenine dinucleotide catalyzed by said enzyme dehydrogenase to subtantially consume the endogenous material or derivative by conversion thereof to an oxidation product of the reaction with the production of reduced beta-nicotinamide adenine dinucleotide, reacting the resulting reduced beta-nicotinamide adenine dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase enzymatic activity in said fluid, and thereafter producing in said fluid a quantity of said compound produced in the course of the determination for said reaction thereof and production of reduced beta-nicotinamide adenine dinucleotide proportionally to the content of said substance.

2. A method as defined in claim 1 wherein said biological fluid is human blood serum.

3. A method as defined in claim 1 wherein the lactate dehydrogenase activity is inhibited by the anion of oxamic acid.

4. A method for determining alpha-amylase present in a biological fluid also containing endogenous glucose, which comprises the steps of:

(1) enzymatically hydrolyzing water-soluble starch with the alpha-amylase present in said fluid to produce oligosaccharides including maltose, (2)(a) concurrently consuming the glucose present in said fluid by reacting the glucose present in said fluid with adenosine triphosphate in the presence of hexokinase to convert the glucose to glucose-6-phosphate, and reacting the glucose-6-phosphate with beta-nicotinamide adenine dinucleotide in the presence of glucose-6-phosphate dehydrogenase to convert the glucose-6-phosphate to 6-phosphogluconate with the production of reduced beta-nicotinamide adenine dinucleotide, and (b) reacting the reduced beta-nicotinamide adenine dinucleotide in said fluid with pyruvate in the presence of lactate dehydrogenase to return the beta-nicotinamide adenine dinucleotide to its oxidized form and produce lactate, (3) thereafter inhibiting the lactate dehydrogenase enzymatic activity in said fluid, and (4) thereafter continuing said hydrolysis with the ampha-amylase present in said fluid, enzymatically hydrolyzing the maltose produced in the presence of alpha-glucosidase to produce glucose, reacting the glucose thus produced with adenosine triphosphate in the presence of hexokinase to produce glucose-6-phosphate, and reacting the glucose-6-phosphate thus produced with beta-nicotinamide adenine dinucleotide in the presence of glucose-6-phosphate dehydrogenase to produce reduced beta-nicotinamide adenine dinucleotide in an amount proportional to the alpha-amylase activity.

5. A method as defined in claim 4 wherein the anion of oxamic acid is added in step (3) to inhibit said activity.

6. A method as defined in claim 4 wherein said biological fluid is human blood serum.

7. A method as defined in claim 6 wherein steps (1) and (2) are conducted together at about 37° C. for about 10 minutes.

8. A method as defined in claim 4 or 7 wherein said fluid is admixed with water-soluble starch, adenosine triphosphate, hexokinase, beta-nicotinamide adenine dinucleotide, glucose-6-phosphate dehydrogenase, a water-soluble salt of pyruvic acid, and lactate dehydrogenase for conducting steps (1) and (2), and the product of steps (1) and (2) is admixed with a water-soluble salt of oxamic acid and with alpha-glucosidase for conducting steps (3) and (4).

9. A method for determining alpha-amylase present in a biological fluid also contacting endogenous glucose, which comprises the steps of:

(1)(a) consuming the glucose present in said fluid by reacting the glucose present in said fluid with adenosine triphosphate in the presence of hexokinase to convert the glucose to glucose-6-phosphate, and reacting the glucose-6-phosphate with beta-nicotinamide adenine dinucleotide in the presence of glucose-6-phosphate dehydrogenase to convert the glucose-6-phosphate to 6-phosphogluconate with the production of reduced beta-nicotinamide adenine dinucleotide, and (b) reacting the reduced beta-nicotinamide adenine dinucleotide in said fluid with pyruvate in the presence of lactate dehydrogenase to return the beta-nicotinamide adenine dinucleotide to its oxidized form and produce lactate, (2) thereafter inhibiting the lactate dehydrogenase enzymatic activity in said fluid, and (3) thereafter enzymatically hydrolyzing soluble starch with the alpha-amylase present in said fluid to produce oligosaccharides including maltose, enzymatically hydrolyzing the maltose produced in the presence of alpha-glucosidase to produce glucose, reacting the glucose thus produced with adenosine triphosphate in the presence of hexokinase to produce glucose-6-phosphate, and reacting the glucose-6-phosphate thus produced with beta-nicotinamide adenine dinucleotide in the presence of glucose-6-phosphate dehydrogenase to produce reduced beta-nicotinamide adenine dinucleotide in an amount proportional to the alpha-amylase activity.

10. A method as defined in claim 9 wherein the anion of oxamic acid is added in step (2) to inhibit said activity.

11. A method for determining triglycerides present in a biological fluid also contacting endogenous glycerol, which comprises the steps of:

(1)(a) consuming the glycerol present in said fluid by reacting the glycerol with beta-nicotinamide adenine dinucleotide in the presence of glycerol dehydrogenase to convert the glycerol to dihydroxyacetone with the production of reduced beta-nicotinamide adenine dinucleotide, and (b) reacting the reduced beta-nicotinamide adenine dinucleotide in said fluid with pyruvate in the presence of lactate dehydrogenase to return the beta-nicotinamide adenine dinucleotide to its oxidized form and produce lactate, (2) thereafter inhibiting the lactate dehydrogenase enzymatic activity in said fluid, and (3) thereafter enzymatically hydrolyzing the triglycerides in said fluid with lipase to produce glycerol, and reacting the glycerol thus produced with beta-nicotinamide adenine dinucleotide in the presence of glycerol dehydrogenase to produce reduced beta-nicotinamide adenine dinucleotide in an amount proportional to the triglyceride content of said fluid.

12. A method as defined in claim 4 or 7 wherein the anions of oxamic and oxalic acids are added in step (2) to inhibit said activity.

13. A method as defined in claim 12 wherein said biological fluid is human blood serum.

14. A method for determining triglycerides present in a biological fluid also containing endogenous glycerol, which comprises the steps of:

(1)(a) consuming the glycerol present in said fluid by reacting the glycerol with adenosine triphosphate in the presence of glycerokinase to convert the glycerol to glycerol phosphate, reacting the glycerol phosphate with beta-nicotinamide adenine dinucleotide in the presence of glycerophosphate dehydrogenase to convert the glycerol phosphate to dihydroxyacetone phosphate with the production of reduced beta-nicotinamide adenine dinucleotide, and (b) reacting the reduced beta-nicotinamide adenine dinucleotide in said fluid with pyruvate in the presence of lactate dehydrogenase to return the beta-nicotinamide adenine dinucleotide to its oxidized form and produce lactate, (2) thereafter inhibiting the lactate dehydrogenase enzymatic activity in said fluid, and (3) thereafter enzymatically hydrolyzing the triglycerides in said fluid with lipase to produce glycerol, reacting the glycerol thus produced with adenosine triphosphate in the presence of glycerokinase to produce glycerol phosphate, and reacting the glycerol phosphate thus produced with beta-nicotinamide adenine dinucleotide in the presence of glycerophosphate dehydrogenase to produce reduced beta-nicotinamide adenine dinucleotide in an amount proportional to the triglyceride content of said fluid.

15. In a method for determining the alpha-amylase present in a biological fluid by reacting glucose-6-phosphate produced in the course of the determination in an oxidation-reduction reaction with beta-nicotinamide adenine dinucleotide in the presence of glucose-6-phosphate dehydrogenase to produce reduced beta-nicotinamide adenine dinucleotide in an amount proportional to the activity of the alpha-amylase in the fluid, said fluid also contacting an endogenous material which or a derivative of which produced during the determination likewise reacts in an oxidation-reduction reaction with beta-nicotinamide adenine dinucleotide in the presence of glucose-6-phosphate dehydrogenase to produce reduced beta-nicotinamide adenine dinucleotide, thereby interfering with the determination, the improvement for obviating the interference caused by the endogenous material which comprises:

reacting said endogenous material or derivative thereof present in said fluid in an oxidation-reduction reaction with beta-nicotinamide adenine dinucleotide in the presence of glucose-6-phosphate dehydrogenase to consume the endogenous material or derivative by conversion thereof to an oxidation product of the reaction with the production of reduced beta-nicotinamide adenine dinucleotide, reacting the resulting reduced beta-nicotinamide adenine dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase enzymatic activity in said fluid, and thereafter producing in said fluid a quantity of glucose-6-phosphate for said reaction thereof and production of reduced beta-nicotinamide adenine dinucleotide in an amount proportional to the alpha-amylase activity.

16. In a method for determining a transaminase present in a biological fluid by reacting L-glutamate produced in the course of the determination in an oxidation-reduction reaction with beta-nicotinamide adenine dinucleotide in the presence of glutamate dehydrogenase to produce reduced beta-nicotinamide adenine dinucleotide in an amount proportional to the activity of the transaminase in the fluid, said fluid also containing an endogenous material which or a derivative of which produced during the determination likewise reacts in an oxidation-reduction reaction with beta-nicotinamide adenine dinucleotide in the presence of glutamate dehydrogenase to produce reduced beta-nicotinamide adenine dinucleotide, thereby interfering with the determination, the improvement for obviating the interference caused by the endogenous material which comprises:

reacting said endogenous material or derivative thereof present in said fluid in an oxidation-reduction reaction with beta-nicotinamide adenine dinucleotide in the presence of glutamate dehydrogenase to consume the endogenous material or derivative by conversion thereof to an oxidation product of the reaction with the production of reduced beta-nicotinamide adenine dinucleotide, reacting the resulting reduced beta-nicotinamide dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase enzymatic activity in said fluid, and thereafter producing in said fluid a quantity of L-glutamate for said reaction thereof and production of reduced beta-nicotinamide adenine dinucleotide in an amount proportional to the transaminase activity.

17. In a method for determining triglycerides present in a biological fluid by reacting glycerol produced in the course of the determination in an oxidation-reduction reaction with beta-nicotinamide adenine dinucleotide in the presence of glycerol dehydrogenase to produce reduced beta-nicotinamide adenine dinucleotide in an amount proportional to the content of the triglycerides in the fluid, said fluid also containing an endogenous material which or a derivative of which produced during the determination likewise reacts in an oxidation-reduction reaction with beta-nicotinamide adenine dinucleotide in the presence of glycerol dehydrogenase to produce reduced beta-nicotinamide adenine dinucleotide, thereby interfering with the determination, the improvement for obviating the interference caused by the endogeneous material which comprises:

reacting said endogeneous material or derivative thereof present in said fluid in an oxidation-reduction reaction with beta-nicotinamide adenine dinucleotide in the presence of glycerol dehydrogenase to consume the endogenous material or derivative by conversion thereof to an oxidation product of the reaction with the production of reduced beta-nicotinamide adenine dinucloeotide, reacting the resulting reduced beta-nicotinamide adenine dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase enzymatic activity in said fluid, and thereafter producing in said fluid a quantity of glycerol for said reaction thereof and production of reduced beta-nicotinamide adenine dinucleotide in an amount proportional to the triglyceride content.

18. In a method for determining triglycerides present in a biological fluid by reacting glycerol phosphate produced in the course of the determination in an oxidation-reduction reaction with beta-nicotinamide adenine dinucleotide in the presence of glycerophosphate dehydrogenase to produce reduced beta-nicotinamide adenine dinucleotide in an amount proportional to the content of the triglycerides in the fluid, said fluid also containing an endogenous material which or a derivative of which produced during the determination likewise reacts in an oxidation-reduction reaction with beta-nicotinamide adenine dinucleotide in the presence of glycerophosphate dehydrogenase to produce reduced beta-nicotinamide adenine dinucleotide, thereby interfering with the determination, the improvement for obviating the interference caused by the endogenous material which comprises:

reacting said endogenous material or derivative thereof present in said fluid in an oxidation-reduction reaction with beta-nicotinamide adenine dinucleotide in the presence of glycerophosphate dehydrogenase to consume the endogenous material or derivative by conversion thereof to an oxidation product with the production of reduced beta-nicotinamide adenine dinucleotide, reacting the resulting reduced beta-nicotinamide adenine dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase enzymatic activity in said fluid, and thereafter producing in said fluid a quantity of glycerol phosphate for said reaction thereof and production of reduced beta-nicotinamide adenine dinucleotide in an amount proportional to the triglyceride content.

19. A two-reagent assay system for determining alpha-amylase present in a biological fluid also containing endogenous glucose, which system includes a first reagent comprising water-soluble starch, adenosine triphosphate, hexokinase, beta-nicotinamide adenine dinucleotide, glucose-6-phosphate dehydrogenase, a water-soluble salt of pyruvic acid, and lactate dehydrogenase, said first reagent to be admixed with said fluid initially for hydrolysis of starch and conversion of glucose present to 6-phosphogluconate in a product containing the beta-nicotinamide adenine dinucleotide in its oxidized form, and a second reagent comprising a water-soluble salt of oxamic acid and alpha-glucosidase, said second reagent to be admixed with said product for inhibiting the enzymatic activity of said lactate dehydrogenase and then producing reduced beta-nicotinamide adenine dinucleotide in an amount proportional to the alpha-amylase activity.

20. A two-reagent assay system for determining alpha-amylase present in a biological fluid also containing endogenous glucose, which system includes a first reagent comprising an aqueous solution of the following materials in proportions per liter of solution between about 80% and 120% of the proportions indicated:

| Materials | Amount |
| --- | --- |
| Water-soluble starch | 1.25 grams |
| Adenosine triphosphate | 1.25 millimoles |
| Beta-nicotinamide adenine dinucleotide | 2 millimoles |
| Alkali metal pyruvate | 0.75 millimoles |
| Hexokinase | 1500 I.U. |
| Glucose-6-phosphate dehydrogenase | 2500 I.U. |
| Lactate dehydrogenase | 250 I.U. |
| Alkali metal phosphate buffer, pH 6.3-7.1 | 25 millimoles |
| Alkali metal chloride | 50 millimoles |
| Magnesium salt | 3 millimoles | said first reagent to be admixed with said fluid initially for hydrolyzing the starch and converting glucose present to 6-phosphogluconate in a product containing the beta-nicotinamide adenine dinucleotide in its oxidized form, and a second reagent comprising an aqueous solution of the following materials in proportions per liter of solution between about 80% and 120% of the proportions indicated:

| Material | Amount |
| --- | --- |
| Alpha-glucosidase | 7000 I.U. |
| Alkali metal oxamate | 180 millimoles |
| Alkali metal phosphate buffer, pH 6.3-7.1 | 25 millimoles | said second reagent to be admixed with said product for inhibiting the enzymatic activity of said lactate dehydrogenase and then producing reduced beta-nicotinamide adenine dinucleotide in an amount proportional to the alpha-amylase activity.

21. An assay system as defined in claim 15 wherein each of said reagents has a pH of about 6.5.

* * * * *